(12) United States Patent
Waugh

(10) Patent No.: US 8,518,414 B2
(45) Date of Patent: Aug. 27, 2013

(54) COMPOSITIONS AND METHODS OF TOPICAL APPLICATION AND TRANSDERMAL DELIVERY OF BOTULINUM TOXINS WITH REDUCED NON-TOXIN PROTEINS

(75) Inventor: Jacob M. Waugh, Mountain View, CA (US)

(73) Assignee: Revance Therapeutics, Inc., Newark, CA (US)

( * ) Notice: Subject to any disclaimer, the term of this patent is extended or adjusted under 35 U.S.C. 154(b) by 42 days.

(21) Appl. No.: 12/093,442

(22) PCT Filed: Nov. 16, 2006

(86) PCT No.: PCT/US2006/060979
§ 371 (c)(1),
(2), (4) Date: Oct. 7, 2008

(87) PCT Pub. No.: WO2007/059528
PCT Pub. Date: May 24, 2007

(65) Prior Publication Data
US 2009/0163412 A1    Jun. 25, 2009

Related U.S. Application Data

(60) Provisional application No. 60/738,144, filed on Nov. 17, 2005.

(51) Int. Cl.
*A61K 8/64* (2006.01)
(52) U.S. Cl.
USPC .................. 424/239.1; 424/178.1; 424/94.63; 514/1.1
(58) Field of Classification Search
None
See application file for complete search history.

(56) References Cited

U.S. PATENT DOCUMENTS

| | | | |
|---|---|---|---|
| 4,078,060 A | 3/1978 | Benson et al. | |
| 4,434,228 A | 2/1984 | Swann | |
| 4,816,568 A | 3/1989 | Hamilton, Jr. et al. | |
| 5,252,713 A | 10/1993 | Morgan, Jr. et al. | |
| 5,420,105 A | 5/1995 | Gustavson et al. | |
| 5,512,547 A | 4/1996 | Johnson et al. | |
| 5,607,691 A | 3/1997 | Hale et al. | |
| 5,629,020 A | 5/1997 | Leone-Bay et al. | |
| 5,668,255 A * | 9/1997 | Murphy | 530/350 |
| 5,709,861 A | 1/1998 | Santiago et al. | |
| 5,744,166 A | 4/1998 | Illum | |
| 5,747,641 A | 5/1998 | Frankel et al. | |
| 5,756,468 A | 5/1998 | Johnson et al. | |
| 5,766,605 A | 6/1998 | Sanders et al. | |
| 5,795,587 A | 8/1998 | Gao et al. | |
| 5,804,604 A | 9/1998 | Frankel et al. | |
| 5,985,434 A | 11/1999 | Qin et al. | |
| 6,217,912 B1 | 4/2001 | Park et al. | |
| 6,280,937 B1 | 8/2001 | Luo et al. | |
| 6,306,423 B1 | 10/2001 | Donovan et al. | |
| 6,312,708 B1 | 11/2001 | Donovan | |
| 6,383,509 B1 | 5/2002 | Donovan et al. | |
| 6,413,941 B1 | 7/2002 | Garnett et al. | |
| 6,447,787 B1 * | 9/2002 | Gassner et al. | 424/247.1 |
| 6,458,763 B1 * | 10/2002 | Peterson et al. | 424/423 |
| 6,495,663 B1 | 12/2002 | Rothbard et al. | |
| 6,506,399 B2 | 1/2003 | Donovan | |
| 6,544,548 B1 | 4/2003 | Siller-Jackson et al. | |
| 6,585,993 B2 | 7/2003 | Donovan et al. | |
| 6,593,292 B1 | 7/2003 | Rothbard et al. | |
| 6,610,820 B1 | 8/2003 | Bonny | |
| 6,645,501 B2 | 11/2003 | Dowdy | |
| 6,669,951 B2 | 12/2003 | Rothbard et al. | |
| 6,670,322 B2 | 12/2003 | Goodnough et al. | |
| 6,680,301 B2 | 1/2004 | Berg et al. | |
| 6,683,049 B1 | 1/2004 | Aoki et al. | |
| 6,692,911 B2 | 2/2004 | Pack et al. | |
| 6,696,038 B1 | 2/2004 | Mahato et al. | |
| 6,730,293 B1 | 5/2004 | Rothbard et al. | |
| 6,759,387 B2 | 7/2004 | Rothbard et al. | |
| 6,831,059 B2 | 12/2004 | Donovan | |

(Continued)

FOREIGN PATENT DOCUMENTS

| | | |
|---|---|---|
| EP | 1005867 | 6/2000 |
| EP | 1180524 | 2/2002 |

(Continued)

OTHER PUBLICATIONS

Somerman et al (Calcif. Tissue Int., 1988, 43:50-53).*

(Continued)

*Primary Examiner* — Albert Navarro
*Assistant Examiner* — Ginny Portner
(74) *Attorney, Agent, or Firm* — Kenneth H. Sonnenfeld; Joseph D. Eng, Jr.; King & Spalding LLP

(57) ABSTRACT

This invention relates to novel compositions of *botulinum* toxin that can be applied topically for various therapeutic, aesthetic and/or cosmetic purposes. The compositions may include *botulinum* toxin complexes, wherein the amounts of hemagglutinin, non-toxin non-hemagglutinin and/or exogenous albumin are selectively and independently reduced compared to conventional commercially available *botulinum* toxin. The compositions may further contain molecules that are not native to *botulinum* toxin and that bind non-covalently to the *botulinum* toxin complexes, thereby acting as skin-tropic "adhesion molecules" to improve the ability of the toxin complexes to adhere to and to penetrate the skin epithelium. The compositions have an improved safety profile compared to existing *botulinum*-containing compositions that are injected subcutaneously. Methods for the use of such compositions are also contemplated by this invention.

16 Claims, No Drawings

(56) References Cited

U.S. PATENT DOCUMENTS

| | | | |
|---|---|---|---|
| 6,866,856 B2 | 3/2005 | Lu et al. | |
| 6,896,886 B2 | 5/2005 | Aoki et al. | |
| 6,974,578 B1 | 12/2005 | Aoki et al. | |
| 7,008,924 B1 | 3/2006 | Yan et al. | |
| 7,056,656 B1 | 6/2006 | Rana et al. | |
| 7,060,498 B1 | 6/2006 | Wang | |
| 7,473,559 B2 | 1/2009 | Lee | |
| 8,124,074 B2* | 2/2012 | Foster et al. | 424/94.63 |
| 2001/0024716 A1 | 9/2001 | Chen et al. | |
| 2002/0006905 A1 | 1/2002 | Aoki et al. | |
| 2002/0009491 A1 | 1/2002 | Rothbard et al. | |
| 2002/0086036 A1 | 7/2002 | Walker | |
| 2002/0107199 A1 | 8/2002 | Walker | |
| 2002/0127247 A1 | 9/2002 | Steward et al. | |
| 2002/0131965 A1 | 9/2002 | Rothbard et al. | |
| 2003/0022831 A1 | 1/2003 | Rothbard et al. | |
| 2003/0027752 A1 | 2/2003 | Steward et al. | |
| 2003/0032593 A1 | 2/2003 | Wender et al. | |
| 2003/0083256 A1 | 5/2003 | Rothbard et al. | |
| 2003/0104622 A1 | 6/2003 | Robbins et al. | |
| 2003/0113349 A1 | 6/2003 | Coleman | |
| 2003/0118598 A1 | 6/2003 | Hunt | |
| 2003/0129194 A1* | 7/2003 | Mazess et al. | 424/178.1 |
| 2003/0138437 A1 | 7/2003 | Hunt | |
| 2003/0147921 A1 | 8/2003 | Goodnough et al. | |
| 2003/0157134 A1 | 8/2003 | Aoki et al. | |
| 2003/0162719 A1 | 8/2003 | Rothbard et al. | |
| 2003/0165567 A1 | 9/2003 | Mixson | |
| 2003/0185788 A1 | 10/2003 | Rothbard et al. | |
| 2003/0215395 A1 | 11/2003 | Yu et al. | |
| 2003/0215412 A1 | 11/2003 | Waugh | |
| 2003/0219462 A1 | 11/2003 | Steward et al. | |
| 2003/0220480 A1 | 11/2003 | Bonny | |
| 2004/0009180 A1 | 1/2004 | Donovan | |
| 2004/0009469 A1 | 1/2004 | Apt et al. | |
| 2004/0013687 A1 | 1/2004 | Simpson | |
| 2004/0013692 A1 | 1/2004 | Aoki et al. | |
| 2004/0033241 A1 | 2/2004 | Donovan | |
| 2004/0037853 A1 | 2/2004 | Borodic | |
| 2004/0109866 A1* | 6/2004 | Chumas et al. | 424/178.1 |
| 2004/0127556 A1 | 7/2004 | Lu et al. | |
| 2004/0136959 A1* | 7/2004 | Puri | 424/93.2 |
| 2004/0147443 A1 | 7/2004 | Renault | |
| 2004/0161405 A9 | 8/2004 | Rothbard et al. | |
| 2004/0186045 A1 | 9/2004 | Rothbard et al. | |
| 2004/0192754 A1 | 9/2004 | Shapira et al. | |
| 2004/0220100 A1 | 11/2004 | Waugh et al. | |
| 2004/0220386 A1 | 11/2004 | Steward et al. | |
| 2004/0247614 A1 | 12/2004 | Dorr et al. | |
| 2004/0247623 A1 | 12/2004 | Cady | |
| 2004/0265935 A1 | 12/2004 | Atassi | |
| 2005/0074461 A1 | 4/2005 | Donovan | |
| 2005/0106182 A1* | 5/2005 | Li et al. | 424/239.1 |
| 2005/0112146 A1 | 5/2005 | Graham | |
| 2005/0129677 A1* | 6/2005 | Li et al. | 424/130.1 |
| 2005/0175636 A1 | 8/2005 | Donovan | |
| 2005/0196414 A1* | 9/2005 | Dake et al. | 424/239.1 |
| 2005/0232966 A1 | 10/2005 | Hughes | |
| 2005/0238667 A1 | 10/2005 | Hunt | |
| 2006/0018931 A1 | 1/2006 | Taylor | |
| 2006/0024331 A1* | 2/2006 | Fernandez-Salas et al. | 424/239.1 |
| 2006/0040882 A1 | 2/2006 | Chen | |
| 2008/0161543 A1* | 7/2008 | Steward et al. | 530/402 |
| 2011/0262423 A1* | 10/2011 | Madec et al. | 424/94.63 |

FOREIGN PATENT DOCUMENTS

| | | |
|---|---|---|
| EP | 1 185291 | 3/2002 |
| EP | 1421948 | 5/2004 |
| EP | 1477183 | 11/2004 |
| EP | 0737074 | 10/2006 |
| WO | WO 92/07871 | 5/1992 |
| WO | WO 94/04686 | 3/1994 |
| WO | WO 97/40854 | 11/1997 |
| WO | WO 98/19710 | 5/1998 |
| WO | WO 00/24419 | 5/2000 |
| WO | WO 00/32764 | 6/2000 |
| WO | WO 00/34308 | 6/2000 |
| WO | WO 01/13957 | 3/2001 |
| WO | WO 0162297 | 8/2001 |
| WO | WO 02/07773 | 1/2002 |
| WO | WO 02/065986 | 8/2002 |
| WO | WO 02/067917 | 9/2002 |
| WO | WO 02/069930 | 9/2002 |
| WO | 02/746497 | * 10/2002 |
| WO | WO 03/049772 | 6/2003 |
| WO | WO 03/072049 | 9/2003 |
| WO | WO 03/097107 | 11/2003 |
| WO | WO 2005/084410 | 9/2005 |
| WO | WO 2006/005910 | 1/2006 |

OTHER PUBLICATIONS

Yano et al., "Control of Hair Growth and Follicle Size by VEGF-Mediated Angiogensis," J. Clin. Invest., 107:409-417, 2001.

Morris et al., "A Peptide Carrier for the Delivery of Biologically Active Proteins into Mammalian Cells," Nature Biotechnology, vol. 19, Dec. 1, 2001, pp. 1173-1176.

Chen, "Biophysical Characterization of the Stability of the 150-Kilodalton Botulinum Toxin, the Nontoxic Component, and the 900-Kilodalton Botulinum Toxin Complex Species," Infection and Immunity. Jun. 1998, vol. 66, No. 6, pp. 2420-2425.

Glogau, "Topically Applied Botulinum Toxin Type A for the Treatment of Primary Axillary Hyperhidrosis: Results of a Randomized, Blinded, Vehicle-Controlled Study," Dermatologic Surgery: Official Publication for American Society for Dermatologic Surgery, Jan. 2007, vol. 33, No. 1, pp. S76-S80.

Supplementary European Search Report dated Dec. 22, 2009 in corresponding European Application No. 06846323.

Fedarko et al., "Factor H Binding to Bone Sialoprotein and Osteopontin Enables Tumor Cell Evasion of Complement-mediated Attack," The Journal of Biological Chemistry, 275(22), pp. 16666-16672.

Fujisawa et al., "Further Characterization of Interaction between Bone Sialoprotein (BSP) and Collagen," Calcification Tissue International, 56, pp. 140-144, 1995.

Revance Therapeutics, Inc., Notification of the Second Office Action for Chinese Patent Application No. 200680050584.7 received from the State Intellectual Property Office of the People's Republic of China, Sep. 9, 2011, 6 pages total.

Title: 1992 Sigma Catalog, pp. 1745.

Title: Mammalian Expression, Publ: 1998 Promega Catalog, pp. 262-265.

Author: Ambache, N., Title: A further survey of the action of clostridium botulinum toxins upon different types of automatic nerve fibre, Publ: J. Physiol, vol. 113, pp. 1-17, 1951.

Author: Bermann I., et al., Title: Selective degeneration of sudomotor fibers in Ross Syndrome and successful treatment of compensatory hyperhidrosis with botulinum toxins, Publ: Muscle & Nerve, vol. 21(12), pp. 1790-1793, 1998.

Author: Blanes-Mira et al., Title: Identification of SNARE complex Modulators that Inhibit Exocytosis from an Alpha-Helix-Constrained Combinatorial Library, Publ: Biochem. J., vol. 375(1), pp. 159-166, Oct. 1, 2003.

Author: Blanes-Mira et al., Title: Small peptides after the N-Terminus domain of SNAP25 Inhibit Snare complex assembly and regulated exocytosis, Publ: J. of Neurochem, vol. 88(1), pp. 124-135, Jan. 2004.

Author: Blanes-Mira et al., Title: A Synthetic Hexapeptide *Argireline) with Antiwrinkle Activity, Publ: Int'l J. of Cosmetic Science, vol. 24(5), pp. 303-310, 2002.

Author: Console et al., Title: Antennapedia and HIV Transactivator of Transcription (TAT) Promote Endocytosis of High Molecular Weight Cargo Upon Binding to Cell Surface Clycosaminoglycans, Publ: J. Biol. Chem., vol. 278(37), pp. 35109-35114, 2003.

Author: Christiano et al., Title: Hepatic gene therapy: Efficient gene delivery and expression in primary hepatocytes utilizing a conjugated adenovirus-DNA complex, Publ: Proc. Nat'l Acad. Sci., pp. 11548-11552, Dec. 1993.

Author: Crosland et al., Title: Detection of Sparse Botulinum Toxin A Binding Sites Using Flourescent Latex Microspheres, Publ: J. of Histotechnology., vol. 22(2), pp. 113-115, Jun. 1999.

Author: Fisher et al., Title: Matrix Sialoprotein of Developing Bone, Publ: J. Biol. Chem., vol. 258, pp. 12723-12727, Oct. 1983.

Author: GenBank Accession No. M77788, pp. 2005, Jun. 21, 2005.

Author: Glogau, R., Title: Botulinum Toxin A neurotoxin for axillary hyperhidrosis-no sweat Botox, Publ: Dermatol. Surg., vol. 24(8), pp. 817-819, 1998.

Author: Heckman, M. et al., Title: Botulinum toxin for axillary hyperhidrosis (excessive sweating), Publ: N. Engl. J. Med., vol. 344(7), 2001.

Author: Kalderon et al., Title: A Short Amino Acid Sequence Able to Specify Nuclear Location, Publ: Cell, vol. 39, pp. 499-509, Dec. 1984.

Author: Lim, E. et al., Title: Topical botulinum toxin to treat hyperhidrosis? No sweat!, Publ: Medical Hypotheses, vol. 67(1), pp. 27-32, 2006.

Author: Nauman, M. et al., Title: Focal Hyperhidrosis—Effective treatment with Intracutaneous botulinum Toxin, Publ: Arch Dermatol., vol. 134, pp. 301-304, 1998.

Author: Naver H., Title: The treatment of focal hyperhidrosis with botulinum toxin, Publ: Eur. J. Neurol., vol. 4(2), pp. S75-S79, 1997.

Author: Odderson, I., Title: Axillary hyperhidrosis: Treatment with Botulinum Toxin A, Publ: Arch. Phys. Med. Rehabil., vol. 79(3), pp. 350-352, 1998.

Author: Printout of Website on Jul. 20, 2005, Title: Botulinum cream.

Author: Puls et al., Title: Gene transfer and expression of a non-viral polycation-based vector in CD4 cells, Publ: Gene Therapy., pp. 1774-1778, Oct. 1, 1999.

Author: Retrieved from internet, Title: http://www.genlantis.com/catalog/product_line.cfm?product_family_key=13&product_line_key=54, Sep. 2, 2005.

Author: Schantz et al., Title: Properties and use of Botulinum Toxin and Other Microbial Neurotoxins in Medicine, Publ: Microbiological Reviews, vol. 56(1), pp. 80-89, Mar. 1992.

Author: Schwartz et al., Title: Peptide-Mediated Celluar Delivery, Publ: Curr. Opin Mol. Ther., vol. 2(2), pp. 162-167, 2000.

Author: Shalaby, Title: Polymers for Augmenting Botulinum Vaccine Efficiency, 1998.

Author: Urbanova et al., Title: Noncovalent interaction of peptides with porphyrins in aqueous solution: conformational study using vibrational CD spectroscopy, Publ: Biopolymers (peptide science), vol. 60, pp. 307-316, 2001.

Author: Voet et al., Publ: Biochemistry, 2nd edition, pp. 1275-1276, 1995.

Author: Wu et al., Title: Receptor-mediated in Vitro Gene Transformation by a Soluable DNA Carrier System, Publ: J. Biol. Chem., vol. 10, pp. 4429-4432, 1987.

\* cited by examiner

COMPOSITIONS AND METHODS OF TOPICAL APPLICATION AND TRANSDERMAL DELIVERY OF BOTULINUM TOXINS WITH REDUCED NON-TOXIN PROTEINS

FIELD OF THE INVENTION

This invention relates to novel compositions of *botulinum* toxin that can be applied topically for various therapeutic, aesthetic and/or cosmetic purposes and that have an improved safety profile compared to existing *botulinum*-containing compositions that are injected subcutaneously.

BACKGROUND OF THE INVENTION

Skin protects the body's organs from external environmental threats and acts as a thermostat to maintain body temperature. It consists of several different layers, each with specialized functions. The major layers include the epidermis, the dermis and the hypodermis. The epidermis is a stratifying layer of epithelial cells that overlies the dermis, which consists of connective tissue. Both the epidermis and the dermis are further supported by the hypodermis, an internal layer of adipose tissue.

The epidermis, the topmost layer of skin, is only 0.1 to 1.5 millimeters thick (Inlander, Skin, New York, N.Y.: People's Medical Society, 1-7 (1998)). It consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the water-holding capacity of keratin. When the horny layer loses its softness and flexibility it becomes rough and brittle, resulting in dry skin.

The dermis, which lies just beneath the epidermis, is 1.5 to 4 millimeters thick. It is the thickest of the three layers of the skin. In addition, the dermis is also home to most of the skin's structures, including sweat and oil glands (which secrete substances through openings in the skin called pores, or comedos), hair follicles, nerve endings, and blood and lymph vessels (Inlander, Skin, New York, N.Y.: People's Medical Society, 1-7 (1998)). However, the main components of the dermis are collagen and elastin.

The hypodermis is the deepest layer of the skin. It acts both as an insulator for body heat conservation and as a shock absorber for organ protection (Inlander, Skin, New York, N.Y.: People's Medical Society, 1-7 (1998)). In addition, the hypodermis also stores fat for energy reserves. The pH of skin is normally between 5 and 6. This acidity is due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

Wrinkles, one of the telltale signs of aging, can be caused by biochemical, histological, and physiologic changes that accumulate from environmental damage to the skin. (Benedetto, International Journal of Dermatology, 38:641-655 (1999)). In addition, there are other secondary factors that can cause characteristic folds, furrows, and creases of facial wrinkles (Stegman et al., The Skin of the Aging Face Cosmetic Dermatological Surgery, $2^{nd}$ ed., St. Louis, Mo.: Mosby Year Book: 5-15 (1990)). These secondary factors include the constant pull of gravity, frequent and constant positional pressure on the skin (e.g., during sleep), and repeated facial movements caused by the contraction of facial muscles (Stegman et al., The Skin of the Aging Face Cosmetic Dermatological Surgery, $2^{nd}$ ed., St. Louis, Mo.: Mosby Year Book: 5-15 (1990)).

Different techniques have been utilized in order to potentially mollify some of the signs of aging. These techniques range from facial moisturizers containing alpha hydroxy acids and retinol to surgical procedures and injections of neurotoxins. For example, in 1986, Jean and Alastair Carruthers, a husband and wife team consisting of an ocuplastic surgeon and a dermatologist, developed a method of using the type A form of *botulinum* toxin for treatment of movement-associated wrinkles in the glabella area (Schantz and Scott, In Lewis GE (Ed) Biomedical Aspects of *Botulinum*, New York: Academic Press, 143-150 (1981)). The Carruthers' use of the type A form of *botulinum* toxin for the treatment of wrinkles led to the seminal publication of this approach in 1992 (Schantz and Scott, In Lewis GE (Ed) Biomedical Aspects of *Botulinum*, New York: Academic Press, 143-150 (1981)). By 1994, the same team reported experiences with other movement-associated wrinkles on the face (Scott, Ophthalmol, 87:1044-1049 (1980)). This in turn led to the birth of the era of cosmetic treatment using the type A form of *botulinum* toxin.

Interestingly, the type A form of *botulinum* toxin is said to be the most lethal natural biological agent known to man. Spores of *C. botulinum* are found in soil and can grow in improperly sterilized and sealed food containers. Ingestion of the bacteria can cause botulism, which can be fatal. *Botulinum* toxin acts to produce paralysis of muscles by preventing synaptic transmission or release of acetylcholine across the neuromuscular junction, and is thought to act in other ways as well. Its action essentially blocks signals that normally would cause muscle spasms or contractions, resulting in paralysis. However, the muscle-paralyzing effects of *botulinum* toxin have been used for therapeutic effects. Controlled administration of *botulinum* toxin has been used to provide muscle paralysis to treat conditions, for example, neuromuscular disorders characterized by hyperactive skeletal muscles. Conditions that have been treated with *botulinum* toxin include hemifacial spasm, adult onset spasmodic torticollis, anal fissure, blepharospasm, cerebral palsy, cervical dystonia, migraine headaches, strabismus, temporomandibular joint disorder, and various types of muscle cramping and spasms. More recently the muscle-paralyzing effects of *botulinum* toxin have been taken advantage of in therapeutic and cosmetic facial applications such as treatment of wrinkles, frown lines, and other results of spasms or contractions of facial muscles.

In addition to the type A form of *botulinum* toxin, there are seven other serologically distinct forms of *botulinum* toxin that are also produced by the gram-positive bacteria *Clostridium botulinum*. Of these eight serologically distinct types of *botulinum* toxin, the seven that can cause paralysis have been designated *botulinum* toxin serotypes A, B, C (also known as C, D, E, F and G. Each of these is distinguished by neutralization with type-specific antibodies. The molecular weight of the *botulinum* toxin protein molecule, for all seven of these active *botulinum* toxin serotypes, is about 150 kD. The different serotypes of *botulinum* toxin vary in the animal species that they affect and in the severity and duration of the paralysis they evoke. For example, it has been determined that *botulinum* toxin type A is 500 times more potent than *botulinum* toxin type B, as measured by the rate of paralysis produced in rats. Additionally, *botulinum* toxin type B has been determined to be non-toxic in primates at a dose of 480 U/kg, about 12 times the primate LD50 for type A. Due to the molecule size and molecular structure of *botulinum* toxin, it cannot cross stratum corneum and the multiple layers of the underlying skin architecture.

As released by *Clostridium botulinum* bacteria, *botulinum* toxin is a component of a toxin complex containing the approximately 150 kD *botulinum* toxin protein molecule along with associated non-toxin proteins. These endogenous non-toxin proteins are believed to include a family of hemagglutinin proteins, as well as non-hemagglutinin protein. The non-toxin proteins are believed to stabilize the *botulinum* toxin molecule in the toxin complex and protect it against denaturation, for example, by digestive acids when toxin complex is ingested. Thus, the non-toxin proteins of the toxin complex protect the activity of the *botulinum* toxin and enhance systemic penetration, particularly when the toxin complex is administered via the gastrointestinal tract. More specifically, it is believed that some of the non-toxin proteins specifically enhance penetration across the gastrointestinal epithelium while other non-toxin proteins stabilize the *botulinum* toxin molecule in blood. Additionally, the presence of non-toxin proteins in the toxin complexes typically causes the toxin complexes to have molecular weights that are greater than that of the bare *botulinum* toxin molecule, which is about 150 kD, as previously noted. For example, *Clostridium botulinum* bacteria can produce *botulinum* type A toxin complexes that have molecular weights of about 900 kD, 500 kD or 300 kD. Interestingly, *botulinum* toxin types B and C are apparently produced as only a 700 kD or a 500 kD complex. *Botulinum* toxin type D is produced as both 300 kD and 500 kD complexes. *Botulinum* toxin types E and F are produced as only approximately 300 kD complexes.

To provide additional stability to *botulinum* toxin, the toxin complexes are often stabilized by combining them with exogenous stabilizers, (e.g., gelatin, polysaccharides, or most commonly additional albumin) during manufacturing. The stabilizers serve to bind and to stabilize toxin complexes in disparate environments, including those associated with manufacturing, transportation, storage, and administration.

Typically, the *botulinum* toxin is administered to patients by carefully controlled injections of compositions containing the *botulinum* toxin complex and albumin, but there are several problems associated with this approach. Not only are the injections painful, but they often must deliver enough toxin to create large subdermal wells of toxin locally around the injection sites, in order to achieve the desired therapeutic or cosmetic effect. Even worse, many injections may be required when the area to be treated is large. Moreover, because the injected toxin complexes contain non-toxin proteins and albumin that stabilize the *botulinum* toxin and increase the molecular weight of the toxin complex, the toxin complexes have a long half-life in the body, are slow to diffuse through tissue, and may cause an undesirable antigenic response in the patient. Also, since the non-toxin proteins and albumin stabilize the *botulinum* toxin in blood, the injections must be carefully placed so that they do not release a large amount of toxin into the bloodstream of the patient, which could lead to fatal systemic poisoning. Thus, injections typically must be performed precisely by highly trained medical professionals with a deep understanding of human anatomy.

In view of all of the problems discussed in the foregoing, it would be highly desirable to have a method of administering *botulinum* toxin that would be painless and require less toxin than conventional injection-based methods. Additionally, it would be highly desirable if such a method were to reduce the antigenicity and blood stability of the *botulinum* toxin, while increasing the diffusion rate of *botulinum* toxin complexes within the body, thereby making it safer to use *botulinum* toxin for various therapeutic, aesthetic and/or cosmetic purposes. It also would be desirable to have a method of administration that does not critically depend on precise injection of the *botulinum* toxin by a medical professional in order to achieve safe administration of the toxin.

SUMMARY OF THE INVENTION

This invention provides a solution to the aforementioned problems by providing a therapeutic *botulinum* toxin composition that can be topically applied to the skin epithelium painlessly and easily. The *botulinum* toxin complexes in the topical compositions of this invention have reduced antigenicity, lower blood stability, a better safety profile, and higher diffusion rates through the skin epithelium compared to conventional commercial *botulinum* toxin complexes that are bound to exogenous albumin (e.g., BOTOX® or MYOBLOC®). Additionally, by using the compositions and associated methods of this invention, less *botulinum* toxin is required to achieve the same clinical result compared to conventional injection-based methods of administration.

One aspect of this invention is the recognition that the endogenous non-toxin proteins in a *botulinum* toxin complex obtained from *Clostridium botulinum* bacteria (viz., the nontoxic hemagglutinin and non-hemagglutinin proteins) undesirably increase the stability and toxicity of the toxin complex, while undesirably decreasing the ability of the toxin to diffuse through the skin epithelium. This invention further recognizes that these effects are exacerbated when an exogenous stabilizer, such as albumin, binds to *botulinum* toxin during conventional manufacturing processes. Thus, one aspect of this invention is to provide *botulinum* toxin complexes wherein the amounts of hemagglutinin, non-toxin non-hemagglutinin and/or exogenous albumin are selectively and independently reduced compared to conventional commercially available *botulinum* toxin (e.g., BOTOX® or MYOBLOC®).

Another aspect of this invention is the recognition that certain non-native molecules (i.e., molecules not found in *botulinum* toxin complexes obtained from *Clostridium botulinum* bacteria) can be added to *botulinum* toxin complexes, and in particular reduced *botulinum* toxin complexes, to improve the ability of the *botulinum* toxin complex to diffuse through the skin epithelium. In a particularly preferred embodiment, the non-native molecules bind non-covalently to the *botulinum* toxin complexes and act as skin-tropic "adhesion molecules" that improve the ability of the toxin complexes to adhere to and to penetrate the skin epithelium, and furthermore reduces the stability of the *botulinum* complex in blood. By way of example, the adhesion molecules may be certain proteins, such as sialoproteins.

Accordingly, one object of this invention is to provide a composition comprising a *botulinum* toxin complex (or a reduced *botulinum* toxin complex) and skin-targeting non-native adhesion molecules that enhance transdermal penetration of the composition for cosmeceutical or therapeutic treatments. The composition optionally may contain added exogenous stabilizers, such as albumin.

The invention further relates to a method for producing a biologic effect by topically applying an effective amount of the compositions within this invention, preferably to the skin, of a subject or patient in need of such treatment. The biologic effect may include, for example, muscle paralysis, reduction of hypersecretion or sweating, treatment of neurologic pain or migraine headache, reduction of muscle spasms, prevention or reduction of acne, reduction or enhancement of an immune response, reduction of wrinkles, or prevention or treatment of various other disorders.

This invention also provides kits for preparing formulations containing a *botulinum* toxin complex (or a reduced *botulinum* toxin complex) and adhesion molecules, or a premix that may in turn be used to produce such a formulation. Also provided are kits that contain means for sequentially administering a *botulinum* toxin complex (or a reduced *botulinum* toxin complex) and adhesion molecules to a subject.

DETAILED DESCRIPTION OF THE INVENTION

This invention relates to novel compositions comprising a *botulinum* toxin, more specifically to such compositions that enable the transport or delivery of a *botulinum* toxin through the skin epithelium (also referred to as "transdermal delivery") with improved skin adherence and penetration, reduced antigenicity and blood stability. The compositions of the invention may be used as topical applications for providing a *botulinum* toxin to a subject, for various therapeutic, aesthetic and/or cosmetic purposes, as described herein. The compositions of the invention also have an improved safety profile over other compositions and methods of delivery of *botulinum* toxin. In addition, these compositions can afford beneficial reductions in immune responses to the *botulinum* toxin.

The term "*botulinum* toxin" as used herein refers to any of the known types of *botulinum* toxin (i.e., the approximately 150 kD *botulinum* toxin protein molecule), whether produced by the bacterium or by recombinant techniques, as well as any such types that may be subsequently discovered including newly discovered serotypes, and engineered variants or fusion proteins. As mentioned above, currently seven immunologically distinct *botulinum* neurotoxins have been characterized, namely *botulinum* neurotoxin serotypes A, B, C, D, E, F and G, each of which is distinguished by neutralization with type-specific antibodies. The *botulinum* toxin serotypes are commercially available, for example, from Sigma-Aldrich (St. Louis, Mo.) and from Metabiologics, Inc. (Madison, Wis.), as well as from other sources. The different serotypes of *botulinum* toxin vary in the animal species that they affect and in the severity and duration of the paralysis they evoke. At least two types of *botulinum* toxin, types A and B, are available commercially in formulations for treatment of certain conditions. Type A, for example, is contained in preparations of Allergan having the trademark BOTOX® and of Ipsen having the trademark DYSPORT®, and type B is contained in preparations of Elan having the trademark MYOBLOC®.

The term "*botulinum* toxin" used in the compositions of this invention can alternatively refer to a *botulinum* toxin derivative, that is, a compound that has *botulinum* toxin activity but contains one or more chemical or functional alterations on any part or on any chain relative to naturally occurring or recombinant native *botulinum* toxins. For instance, the *botulinum* toxin may be a modified neurotoxin that is a neurotoxin which has at least one of its amino acids deleted, modified or replaced, as compared to a native, or the modified neurotoxin can be a recombinantly produced neurotoxin or a derivative or fragment thereof. For instance, the *botulinum* toxin may be one that has been modified in a way that, for instance, enhances its properties or decreases undesirable side effects, but that still retains the desired *botulinum* toxin activity. The *botulinum* toxin may be any of the *botulinum* toxin complexes produced by the bacterium, as described above. Alternatively the *botulinum* toxin used in this invention may be a toxin prepared using recombinant or synthetic chemical techniques, e.g. a recombinant peptide, a fusion protein, or a hybrid neurotoxin, for example prepared from subunits or domains of different *botulinum* toxin serotypes (see U.S. Pat. No. 6,444,209, for instance). The *botulinum* toxin may also be a portion of the overall molecule that has been shown to possess the necessary *botulinum* toxin activity, and in such case may be used per se or as part of a combination or conjugate molecule, for instance a fusion protein. Alternatively, the *botulinum* toxin may be in the form of a *botulinum* toxin precursor, which may itself be non-toxic, for instance a non-toxic zinc protease that becomes toxic on proteolytic cleavage.

The term "*botulinum* toxin complex" or "toxin complex" as used herein refers to the approximately 150 kD *botulinum* toxin protein molecule (belonging to any one of *botulinum* toxin serotypes A-G), along with associated endogenous non-toxin proteins (i.e., hemagglutinin protein and non-toxin non-hemagglutinin protein produced by *Clostridium botulinum* bacteria). Note, however, that the *botulinum* toxin complex need not be derived from *Clostridium botulinum* bacteria as one unitary toxin complex. For example, *botulinum* toxin or modified *botulinum* toxin may be recombinantly prepared first and then subsequently combined with the non-toxin proteins. Recombinant *botulinum* toxin can also be purchased (e.g., from List Biological Laboratories, Campbell, Calif.) and then combined with non-toxin proteins.

This invention also contemplates "reduced *botulinum* toxin complexes", in which the *botulinum* toxin complexes have reduced amounts of non-toxin protein compared to the amounts naturally found in *botulinum* toxin complexes produced by *Clostridium botulinum* bacteria. In one embodiment, reduced *botulinum* toxin complexes are prepared using any conventional protein separation method to extract a fraction of the hemagglutinin protein or non-toxin non-hemagglutinin protein from *botulinum* toxin complexes derived from *Clostridium botulinum* bacteria. For example, reduced *botulinum* toxin complexes may be produced by dissociating *botulinum* toxin complexes through exposure to red blood cells at a pH of 7.3 (e.g., see EP 1514556 A1, hereby incorporated by reference). HPLC, dialysis, columns, centrifugation, and other methods for extracting proteins from proteins can be used. Alternatively, when the reduced *botulinum* toxin complexes are to be produced by combining synthetically produced *botulinum* toxin with non-toxin proteins, one may simply add less hemagglutinin or non-toxin non-hemagglutinin protein to the mixture than what would be present for naturally occurring *botulinum* toxin complexes. Any of the non-toxin proteins (e.g., hemagglutinin protein or non-toxin non-hemagglutinin protein or both) in the reduced *botulinum* toxin complexes according to the invention may be reduced independently by any amount. In certain exemplary embodiments, one or more non-toxin proteins are reduced by at least about 0.5%, 1%, 3%, 5%, 10%, 20%, 30%, 40%, 50%, 60%, 70%, 80%, or 90% compared to the amounts normally found in *botulinum* toxin complexes. *Clostridium botulinum* bacteria produce seven different serotypes of toxin and commercial preparations are manufactured with different relative amounts of non-toxin proteins (i.e. different amount of toxin complexes). For example, Myobloc has 5000 U of *Botulinum* toxin type B per ml with 0.05% human serum albumin, 0.01 M sodium succinate, and 0.1 M sodium chloride. Dysport has 500 U of *botulinum* toxin type A-haemaglutinin complex with 125 mcg albumin and 2.4 mg lactose. In one particularly interesting embodiment, substantially all of the non-toxin protein (e.g., >95% of the hemagglutinin protein and non-toxin non-hemagglutinin protein) that would normally be found in *botulinum* toxin complexes derived from *Clostridium botulinum* bacteria is removed from the *botuli-* num toxin complex. Furthermore, although the amount endogenous non-toxin proteins may be reduced by the same amount in some cases, this invention also contemplates reducing each of the endogenous non-toxin proteins by different amounts, as well as reducing at least one of the endogenous non-toxin proteins, but not the others.

In addition to (or instead of) reducing the amount of endogenous non-toxin protein to destabilize the *botulinum* toxin complex, this invention also contemplates the reducing the amount of exogenous stabilizers that are normally added during manufacturing. An example of such an exogenous stabilizer is albumin, which is normally added during manufacturing to *botulinum* toxin complexes in amount equal to 1000 times the amount of albumin found in the endogenous non-toxin, non-hemagglutinin component of a naturally occurring *botulinum* toxin complex. According to this invention, the amount of added exogenous albumin can be any amount less than the conventional thousand-fold excess of exogenous albumin. In certain exemplary embodiments of the invention, only about 500×, 400×, 300×, 200×, 100×, 50×, 10×, 5×, 1×, 0.5×, 0.1×, or 0.01× the amount of the albumin in naturally occurring *botulinum* toxin complexes is added. In one embodiment, no exogenous albumin is added as a stabilizer to the compositions of the invention. In other embodiments, exogenous stabilizers in addition to (or instead of) albumin are added to the therapeutic topical compositions of the invention. For example, other stabilizers contemplated by the invention include lactose, gelatin and polysaccharides.

An "adhesion molecule" according to this invention may be a protein or other molecule that possesses at least the following properties: (1) it is not found in naturally occurring *botulinum* toxin complexes (i.e., "non-native"); (2) it serves to stabilize *botulinum* toxin complexes or reduced *botulinum* toxin complexes, especially those that have been combined with little or no excess exogenous albumin or other stabilizer; and (3) when mixed with *botulinum* toxin complexes or reduced *botulinum* toxin complexes, it promotes transdermal penetration of the *botulinum* toxin, enabling the toxin to be administered to muscles and/or other skin-associated structures in amounts that are sufficient to produce a desired therapeutic or cosmetic effect. Generally speaking, it is preferable if the transport may occur without covalent modification of the *botulinum* toxin. In certain preferred embodiments, the adhesion molecules are capable of binding to specific components of skin, non-limiting examples of which include keratinocytes, epidermal cells, and hair follicles. By way of example, the adhesion molecules according to the invention may be proteins capable of binding to keratinocyte growth factor, keratinocyte binding proteins, epidermal growth factor (EGF), EGF-like proteins, and neurotrophins such as nerve growth factor, brain-derived neurotrophic factor, neurotrophin-3, and neurotrophin-4/5. In some embodiments of the invention, the therapeutic topical composition includes more than one different type of non-native adhesion molecule.

In one particularly interesting embodiment, the non-native adhesion molecules are sialoproteins. Without wishing to be bound by any particular scientific theory, it is believed that sialoproteins promote skin adherence and transdermal penetration of the *botulinum* toxin, while enhancing stabilization of the *botulinum* toxin in skin and in vitro, and reducing blood and systemic activity for an improved safety profile. Non-limiting examples of sialoproteins contemplated by this invention include bone sialoprotein I (also known as BSPI, bone sialoprotein, osteopontin, OPN, secreted phosphoprotein 1, Spp 1, early T lymphocyte activation protein-1, ETA-1, urinary stone protein, nephropontin) and bone sialoprotein II (also known as BSPII, integrin-binding sialoprotein, cell binding sialoprotein, BNSP). Sialoproteins are commercially available, for example, from Chemicon International. Other adhesion molecules that bind and internalize in the epithelial cells especially skin and bladder epithelial cells can be used. Family of adhesion molecules such as cadherins, integrins, immunoglobulin superfamily, selectins and other transmembrane sialoprotein such as podocalyxin may be added.

Generally speaking, the concentration of adhesion molecules in the compositions according to the invention should be sufficient to allow the *botulinum* toxin to be delivered transdermally. Furthermore, without wishing to be bound by theory, it is believed that the transdermal transport rate follows receptor-mediated kinetics, such that transdermal transport increases with increasing amounts of adhesion molecules up to a saturation point, upon which the transport rate becomes constant. Thus, in a preferred embodiment, the amount of added adhesion molecules is equal to the amount that maximizes transdermal penetration rate right before saturation. A useful concentration range for the adhesion molecules in the topical compositions of this invention is about 0.1 ng to about 1.0 mg per unit of the *botulinum* toxin composition as described herein. More preferably, the adhesion molecules in the topical compositions of the invention are in the range of about 0.1 mg to 0.5 mg per unit of *botulinum* toxin. For example, in the case of bone sialoprotein I, which is an example of a sialoprotein contemplated by the invention, a useful range is between about 0.1 ng and about 1.0 mg, more preferably between about 0.1 mg and about 0.5 mg.

Compositions of this invention are preferably in the form of products to be applied to the skin or epithelium of subjects or patients, i.e. humans or other mammals in need of the particular treatment. The term "in need" is meant to include both pharmaceutical or health-related needs, for example, treating conditions involving undesirable facial muscle spasms, as well as cosmetic and subjective needs, for example, altering or improving the appearance of facial tissue. In general the compositions are prepared by mixing the *botulinum* toxin (either containing the associated non-toxin proteins or reduced associated non-toxin proteins) with the non-native adhesion molecules, and usually with one or more additional pharmaceutically acceptable carriers or excipients. In their simplest form they may contain a simple aqueous pharmaceutically acceptable carrier or diluent, such as buffered saline. However, the compositions may contain other ingredients typical in topical pharmaceutical or cosmeceutical compositions, that is, a dermatologically or pharmaceutically acceptable carrier, vehicle or medium, i.e. a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. As appropriate, compositions of the invention may comprise any ingredient conventionally used in the fields under consideration, and particularly in cosmetics and dermatology.

In terms of their form, compositions of this invention may include solutions, emulsions (including microemulsions), suspensions, creams, lotions, gels, powders, or other typical solid or liquid compositions used for application to skin and other tissues where the compositions may be used. Such compositions may contain, in addition to the *botulinum* toxin and non-native adhesion molecules, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

Compositions according to this invention may be in the form of controlled-release or sustained-release compositions, wherein the *botulinum* toxin and the non-native adhesion molecules are encapsulated or otherwise contained within a material such that they are released onto the skin in a controlled manner over time. The composition comprising the *botulinum* toxin and non-native adhesion molecules may be contained within matrixes, liposomes, vesicles, microcapsules, microspheres and the like, or within a solid particulate material, all of which is selected and/or constructed to provide release of the *botulinum* toxin over time. The *botulinum* toxin and the non-native adhesion molecules may be encapsulated together (e.g., in the same capsule) or separately (in separate capsules).

*Botulinum* toxin can be delivered to muscles underlying the skin, or to glandular structures within the skin, in an effective amount to produce paralysis, produce relaxation, alleviate contractions, prevent or alleviate spasms, reduce glandular output, or other desired effects. Local delivery of the *botulinum* toxin in this manner could afford dosage reductions, reduce toxicity and allow more precise dosage optimization for desired effects relative to injectable or implantable materials.

The compositions of the invention are applied so as to administer an effective amount of the *botulinum* toxin. The term "effective amount" as used herein means an amount of a *botulinum* toxin as defined above that is sufficient to produce the desired muscular paralysis or other biological or aesthetic effect, but that implicitly is a safe amount, i.e. one that is low enough to avoid serious side effects. Desired effects include the relaxation of certain muscles with the aim of, for instance, decreasing the appearance of fine lines and/or wrinkles, especially in the face, or adjusting facial appearance in other ways such as widening the eyes, lifting the corners of the mouth, or smoothing lines that fan out from the upper lip, or the general relief of muscular tension. The last-mentioned effect, general relief of muscular tension, can be effected in the face or elsewhere. The compositions of the invention may contain an appropriate effective amount of the *botulinum* toxin for application as a single-dose treatment, or may be more concentrated, either for dilution at the place of administration or for use in multiple applications. Through the use of the skin-targeting non-native adhesion molecules of this invention, a *botulinum* toxin can be administered transdermally to a subject for treating conditions such as undesirable facial muscle or other muscular spasms, hyperhidrosis, acne, or conditions elsewhere in the body in which relief of muscular ache or spasms is desired. The *botulinum* toxin is administered topically for transdermal delivery to muscles or to other skin-associated structures. The administration may be made, for example, to the legs, shoulders, back (including lower back), axilla, palms, feet, neck, groin, dorsa of the hands or feet, elbows, upper arms, knees, upper legs, buttocks, torso, pelvis, or any other parts of the body where administration of the *botulinum* toxin is desired.

Administration of *botulinum* toxin may also be carried out to treat other conditions, including but not limited to treating neurologic pain, prevention or reduction of migraine headache or other headache pain, prevention or reduction of acne, prevention or reduction of dystonia or dystonic contractions (whether subjective or clinical), prevention or reduction of symptoms associated with subjective or clinical hyperhidrosis, reducing hypersecretion or sweating, reducing or enhancing immune response, or treatment of other conditions for which administration of *botulinum* toxin by injection has been suggested or performed.

Most preferably, the compositions are administered by or under the direction of a physician or other health care professional. They may be administered in a single treatment or in a series of periodic treatments over time. For transdermal delivery of *botulinum* toxin for the purposes mentioned above, a composition as described above is applied topically to the skin at a location or locations where the effect is desired. Because of its nature, most preferably the amount of *botulinum* toxin applied should be applied with care, at an application rate and frequency of application that will produce the desired result without producing any adverse or undesired results. Accordingly, for instance, topical compositions of the invention should be applied at a rate of from about 1 U to about 20,000 U, preferably from about 1 U to about 10,000 U *botulinum* toxin per $cm^2$ of skin surface. Higher dosages within these ranges could preferably be employed in conjunction with controlled release materials, for instance, or allowed a shorter dwell time on the skin prior to removal.

This invention also includes transdermal delivery devices for transmitting *botulinum* toxin-containing compositions described herein across skin. Such devices may be as simple in construction as a skin patch, or may be a more complicated device that includes means for dispensing and monitoring the dispensing of the composition, and optionally means for monitoring the condition of the subject in one or more aspects, including monitoring the reaction of the subject to the substances being dispensed.

The compositions, both in general, and in such devices, can be pre-formulated or pre-installed in the device as such, or can be prepared later, for example using a kit that contains the two ingredients (*botulinum* toxin and non-native adhesion molecules) for combining at or prior to the time of application. The amount of non-native adhesion molecule or the ratio of it to the *botulinum* toxin will depend on which carrier is chosen for use in the composition in question. The appropriate amount or ratio of carrier molecule in a given case can readily be determined, for example, by conducting one or more experiments such as those described below.

In general, the invention also contemplates a method for administering *botulinum* toxin (preferably as reduced *botulinum* toxin complexes) to a subject or patient in need thereof, in which an effective amount of *botulinum* toxin is topically administered in conjunction with adhesion molecules, as described herein. By "in conjunction with" it is meant that the two components (*botulinum* toxin and adhesion molecules) are administered in a combination procedure, which may involve either combining them prior to topical administration to a subject, or separately administering them, but in a manner such that they act together to provide the requisite delivery of an effective amount of the therapeutic protein. For example, a composition containing the adhesion molecules may first be applied to the skin of the subject, followed by applying a skin patch or other device containing the *botulinum* toxin The *botulinum* toxin may be incorporated in dry form in a skin patch or other dispensing device and the adhesion molecules may be applied to the skin surface before application of the patch so that the two act together, resulting in the desired transdermal delivery. In that sense, thus, the two substances (adhesion molecule and *botulinum* toxin) act in combination or perhaps interact to form a composition or combination in situ. Accordingly, the invention also includes a kit with a device for dispensing *botulinum* toxin via the skin and a liquid, gel, cream or the like that contains the adhesion molecules, and that is suitable for applying to the skin or epithelium of a subject. Kits for administering the compositions of the inventions, either under direction of a health care professional or by the patient or subject, may also include a custom applicator suitable for that purpose.

The compositions of this invention are suitable for use in physiologic environments with pH ranging from about 4.5 to about 6.3, and may thus have such a pH. The compositions according to this invention may be stored either at room temperature or under refrigerated conditions.

It is understood that the following examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Transport of a *Botulinum* Toxin in vivo Using Sialoproteins

This experiment demonstrates the use of sialoproteins to transport a large complex containing an intact labeled protein *botulinum* toxin across intact skin after a single time administration.

BOTOX® brand of botulinum toxin type A (Allergan, Irvine, Calif.) is selected for this experiment. The botulinum toxin is reconstituted according to the manufacturer's instructions. An aliquot of the protein is biotinylated with a calculated 12-fold molar excess of sulfo-NHS-LC biotin (Pierce Chemical, Rockford, Ill.). 2.0 units of botulinum toxin per aliquot (i.e., 20 U total) and sialoprotein at a calculated MW ratio of 4:1 are mixed to homogeneity and diluted to 200 microliters with phosphate buffered saline. The resulting composition is mixed to homogeneity with 1.8 ml of CETAPHIL® lotion and aliquoted in 200 microliter portions. Animal Experiment to Determine Transdermal Delivery Efficiencies After Single Time Treatment with *Botulinum* Toxin Composition Containing Sialoproteins:

Animals are anesthetized via inhalation of isoflurane during application of treatments. After being anesthetized, C57BLK/6 mice (n=10) undergo topical application of metered 200 microliter dose of the appropriate treatment applied to the cranial portion of dorsal back skin (selected because the mouse cannot reach this region with mouth or limbs). Animals do not undergo depilation. At 30 minutes after the initial treatment, mice are euthanized via inhalation of $CO_2$, and treated skin segments are harvested at full thickness by blinded observers. Treated segments are divided into three equal portions; the cranial portion was fixed in 10% neutral buffered formalin for 12-16 hours then stored in 70% ethanol until paraffin embedding. The central portion is snap-frozen and employed directly for biotin visualization by blinded observers as summarized below. The treated caudal segment is snap-frozen for solubilization studies.

Biotin visualization is conducted as follows. Briefly, each section is immersed for 1 hour in NeutrAvidin® (Pierce Biotechnology, Rockford, Ill.) buffer solution at room temperature. To visualize alkaline phosphatase activity, cross sections are washed in saline four times then immersed in NBT BCIP (Pierce Biotechnology) for approximately 1 hour. Sections are then rinsed in saline and photographed in entirety on a Nikon E600 microscope with plan-apochromat lenses. Total positive staining is determined by blinded observer via batch image analysis using Image Pro Plus software (Media Cybernetics, Silver Spring, Md.) and is normalized to total cross-sectional area to determine percent positive staining for each. Mean and standard error are subsequently determined for each group with analysis of significance at 95% confidence in one way ANOVA repeated measures using Statview software (Abacus, Berkeley, Calif.). The results demonstrate that sialoproteins allow efficient transfer of *botulinum* toxin after topical administration in a murine model of intact skin.

Example 2

*Botulinum* Toxin Administered Transdermally to Treat Facial Wrinkles

A female wishes to reduce the fine lines that fan out from the left side of her upper lip. A transdermal patch containing a composition containing 1 Unit *botulinum* toxin type A, 0.01 mg sialoprotein, and is essentially free of non-toxin proteins and albumin is applied to the area on her face containing the fine lines. The patch is applied only at night when the subject is asleep. Within 1-7 days the appearance of the fine lines is greatly reduced. This beneficial effect persists with continued application of the patch. The reduced antigenicity as a result of the lack of animal-derived albumin or gelatin allows for repeated use of the *botulinum* toxin composition.

I claim:

1. A method of transdermally administering a botulinum toxin to a subject, the method comprising
topically applying an effective amount of a composition to intact skin in an area in need thereof, the composition comprising
botulinum toxin; and
a sialoprotein adhesion molecule;
wherein the sialoprotein adhesion molecule is present in said composition in an amount from 0.1 ng to 1 mg per unit of botulinum toxin, inclusive; and
wherein the sialoprotein adhesion molecule is selected from the group consisting of bone sialoprotein I and bone sialoprotein II.

2. The method according to claim 1, wherein the sialoprotein adhesion molecule is bone sialoprotein I.

3. The method according to claim 1, wherein the sialoprotein adhesion molecule is bone sialoprotein II.

4. A method of treating a condition by transdermal administration of a botulinum toxin to a subject, said method comprising:
topically applying an effective amount of a composition to an area in need thereof, the composition comprising
botulinum toxin; and
a sialoprotein adhesion molecule;
wherein the sialoprotein adhesion molecule is present in said composition in an amount from 0.1 ng to 1 mg per unit of botulinum toxin, inclusive,
wherein the condition is selected from the group consisting of muscular spasm, clinical or subjective hyperhidrosis, acne, pain, clinical or subjective dystonia, hypersecretion, wrinkles, and an immune disorder; and
wherein the sialoprotein adhesion molecule is selected from the group consisting of bone sialoprotein I and bone sialoprotein II.

5. The method according to claim 4, wherein the sialoprotein adhesion molecule is bone sialoprotein I.

6. The method according to claim 4, wherein the sialoprotein adhesion molecule is bone sialoprotein II.

7. The method according to claim 4, wherein the condition is muscular spasm.

8. The method according to claim 4, wherein the condition is clinical hyperhidrosis.

9. The method according to claim 4, wherein the condition is subjective hyperhidrosis.

10. The method according to claim 4, wherein the condition is acne.

11. The method according to claim 4, wherein the condition is pain.

12. The method according to claim 4, wherein the condition is clinical dystonia.

13. The method according to claim 4, wherein the condition is subjective dystonia.

14. The method according to claim 4, wherein the condition is hypersecretion.

15. The method according to claim 4, wherein the condition is wrinkles.

16. The method according to claim 4, wherein the condition is an immune disorder.

\* \* \* \* \*